US012338429B1

(12) United States Patent
Caldwell et al.

(10) Patent No.: US 12,338,429 B1
(45) Date of Patent: Jun. 24, 2025

(54) DEVICES, SYSTEMS, AND METHODS FOR REHYDRATION OF MICROORGANISMS TO ENHANCE AGRICULTURAL YIELDS

(71) Applicant: 3Bar Biologics, Inc., Columbus, OH (US)

(72) Inventors: Bruce H. Caldwell, Columbus, OH (US); Jane Patterson Fife, Powell, OH (US); Rebecca Williams-Wagner, Lewis Center, OH (US); Matt Sells, Dayton, OH (US); Chris Koenig, Columbus, OH (US)

(73) Assignee: 3Bar Biologics, Inc., Columbus, OH (US)

( * ) Notice: Subject to any disclaimer, the term of this patent is extended or adjusted under 35 U.S.C. 154(b) by 0 days.

(21) Appl. No.: 18/431,281

(22) Filed: Feb. 2, 2024

(51) Int. Cl.

| | |
|---|---|
| ***C12N 1/04*** | (2006.01) |
| ***A01N 63/20*** | (2020.01) |
| ***A01N 63/30*** | (2020.01) |
| ***C12M 1/00*** | (2006.01) |
| ***C12N 1/38*** | (2006.01) |
| *C05F 11/08* | (2006.01) |

(52) U.S. Cl.
CPC ............... *C12N 1/04* (2013.01); *A01N 63/20* (2020.01); *A01N 63/30* (2020.01); *C12M 23/32* (2013.01); *C12M 23/34* (2013.01); *C12N 1/38* (2013.01)

(58) Field of Classification Search
None
See application file for complete search history.

(56) References Cited

U.S. PATENT DOCUMENTS

| | | | | |
|---|---|---|---|---|
| 5,507,133 | A | 4/1996 | Singleton | |
| 6,146,875 | A * | 11/2000 | Ward | C12M 23/14 435/243 |
| 11,812,685 | B1 | 11/2023 | Eviston | |
| 2005/0227269 | A1* | 10/2005 | Lloyd | B01L 3/50825 435/6.1 |
| 2009/0321350 | A1* | 12/2009 | Nelson | C02F 3/34 210/205 |
| 2015/0264938 | A1 | 9/2015 | Gage et al. | |
| 2020/0347336 | A1 | 11/2020 | Caldwell et al. | |
| 2022/0204420 | A1* | 6/2022 | Belcher | C05G 5/23 |
| 2023/0330657 | A1* | 10/2023 | Salter | C12Q 1/689 |

* cited by examiner

*Primary Examiner* — Holly Kipouros
(74) *Attorney, Agent, or Firm* — Billion & Armitage

(57) ABSTRACT

A microorganism activation system for activating microorganisms prior to application of microorganisms to agricultural products includes a first container, a second container, and a disruptable dividing member. The first container includes a stabilized microbial culture therein. The second container includes an aqueous rehydration solution therein. The disruptable dividing member separates the stabilized microbial culture in the first container from the aqueous rehydration solution in the second container. Disrupting the dividing member releases the stabilized microbial culture into the second chamber to contact the aqueous rehydration solution. Contact between the stabilized microbial culture and the aqueous rehydration solution re-initiates cellular activity of the microorganisms.

12 Claims, 6 Drawing Sheets

DEVICES, SYSTEMS, AND METHODS FOR REHYDRATION OF MICROORGANISMS TO ENHANCE AGRICULTURAL YIELDS

BACKGROUND

The present disclosure relates generally to systems and methods for rehydration of beneficial microbial preparations such as plant-growth promoting microbes for use on agricultural products.

The commercialization and distribution of beneficial microbial preparations, such as plant-growth promoting microbes, microbes that increase the nutritional content of soils and help manage water use efficiency, or that control the growth of phytopathogens, may be formulated as transportable, shelf-stable concentrates that support the microbes' functional properties. Stabilization for long-term storage (e.g., via dehydration, including freeze-drying (lyophilization)), exposes the live cells to a variety of stress conditions (e.g., freezing, vacuum, cryoprotectants, and low water activity). In addition, the viability of stabilized microbes can be compromised during and after re-hydration. Rehydration involves an important step in the recovery of dehydrated microbes. Successful rehydration is based on retaining the integrity of the cells as support for the microbes' functionality. Even with careful procedures supporting survival during freezing, drying and storage, an inadequate rehydration step may lead to poor cell viability and a low final survival rate. This is especially important for agricultural use, where a worker unskilled in the microbiological arts may be utilizing a microbial inoculant.

The rehydration step re-initiates cellular functions of the microorganism. For example, the microorganisms may resume synthesizing RNA, enzymes, and essential metabolites that might be missing from their new environment (such as growth factors or macromolecules), adjust to environmental conditions (e.g., temperature, pH, oxygen) and undertake repair of injured cells. The rehydration of microorganisms does not per se initiate fermentation or log phase microbial growth.

Thus, there is a need for materials, systems, and methods to facilitate rehydration of stabilized microbes in the field on-demand by those unskilled in the microbiological arts to improve microbial survival rate and ensure that these beneficial microbes regain their functionality for promoting agricultural plant health, plant nutrition, soil nutritive capacity, optimizing soil moisture status, soil aeration, soil water holding capacity and reducing the susceptibility of plants, to pests, diseases and weeds.

SUMMARY

According to some embodiments, an apparatus for delivering viable microorganisms in an agricultural applicator includes a first container, a second container, and a disruptable dividing member. The first container includes a stabilized microbial culture therein. The second container including an aqueous rehydration solution disposed therein. The disruptable dividing member separates the stabilized microbial culture in the first container from the aqueous rehydration solution in the second container. Disrupting the dividing member forms a flow path between the first container and the second container to allow contact between the stabilized microbial culture and the aqueous rehydration solution. Contact between the stabilized microbial culture and the aqueous rehydration solution re-initiates cellular activity of the viable microorganisms.

According to some embodiments, a microorganism activation system for activating microorganisms prior to application of microorganisms to agricultural products includes a first container, a second container, and a disruptable dividing member. The first container includes a stabilized microbial culture therein. The second container includes an aqueous rehydration solution therein. The disruptable dividing member separates the stabilized microbial culture in the first container from the aqueous rehydration solution in the second container. Disrupting the dividing member releases the stabilized microbial culture into the second chamber to contact the aqueous rehydration solution. Contact between the stabilized microbial culture and the aqueous rehydration solution re-initiates cellular activity of the microorganisms.

According to some embodiments, a method for delivering viable microorganisms to an agricultural applicator includes providing a first container and a second container. The first container includes a stabilized microbial culture therein. The stabilized microbial culture includes microorganisms in an inactive cellular state. The second container includes an aqueous rehydration solution therein. A disruptable dividing member is positioned between the second container and the first container. The method includes disrupting the dividing member to form a flow path between the first container and the second container. The stabilized microbial culture travels through the flow path to contact the aqueous rehydration solution in the second container. The method includes re-initiating a cellular function of the microorganisms with the aqueous rehydration solution in the second container. The microorganisms are in an active cellular state following re-initiation of the cellular function of the microorganisms.

These and other examples and features of the present devices, systems, and methods will be set forth, at least in part, in the following Detailed Description. This Overview is intended to provide non-limiting examples of the present subject matter-it is not intended to provide an exclusive or exhaustive explanation. The Detailed Description below is included to provide further information about the present devices, systems, and methods.

BRIEF DESCRIPTION OF DRAWINGS

This written disclosure describes illustrative embodiments that are non-limiting and non-exhaustive. Reference is made to illustrative embodiments that are depicted in the figures, in which.

DETAILED DESCRIPTION

According to some embodiments, this disclosure relates to materials, kits, systems, and methods for rehydrating and revitalizing inactive microbial cultures prior to applying the microorganisms to agricultural crops to improve plant protection, plant nutrition, and/or plant growth. Embodiments described herein can be utilized/implemented during rehydration of stabilized microbial cultures by any end user, including a person without specialized knowledge of microbial metabolism, or direct access to a microbiology laboratory. The compositions, systems, and methods of use described will facilitate microbial cell conditioning during rehydration for better microbe survival.

Figure 1A:
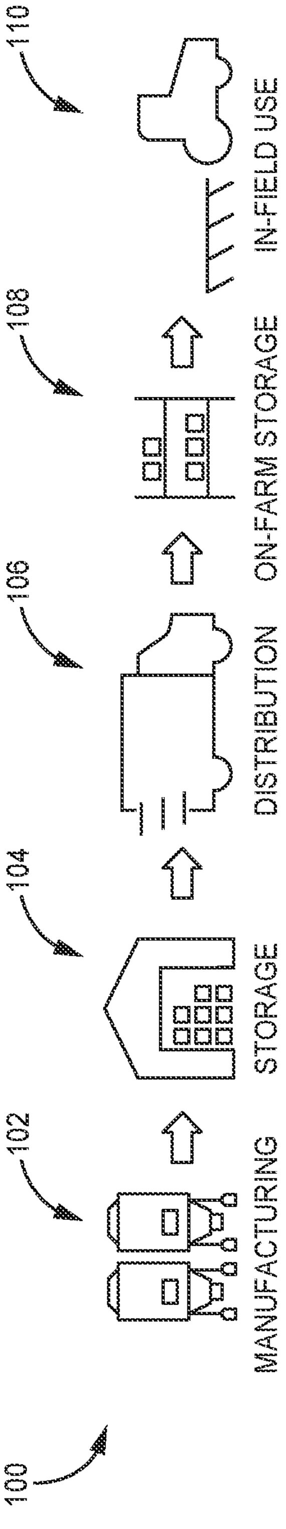
FIG. 1A illustrates a diagrammatic view of an exemplary supply chain of a biologic agricultural product, according to some embodiments.

FIG. 1A illustrates a diagrammatic view of an exemplary supply chain 100 of a biologic agricultural product, according to some embodiments. The supply chain 100 may include a manufacturing stage 102 where the biologic agricultural product is produced. The biologic agricultural product may include microorganisms (i.e., microbes) and a solution to suspend and preserve the microorganisms. The supply chain may include a manufacturing storage stage 104 where the product is stored, a distribution stage 106 where the product is transported to an agricultural location, an on-farm storage stage 108 where the product is stored, and finally an in-field use stage 110 where the biologic agricultural product is applied to crops and/or soil.

Figure 1B:
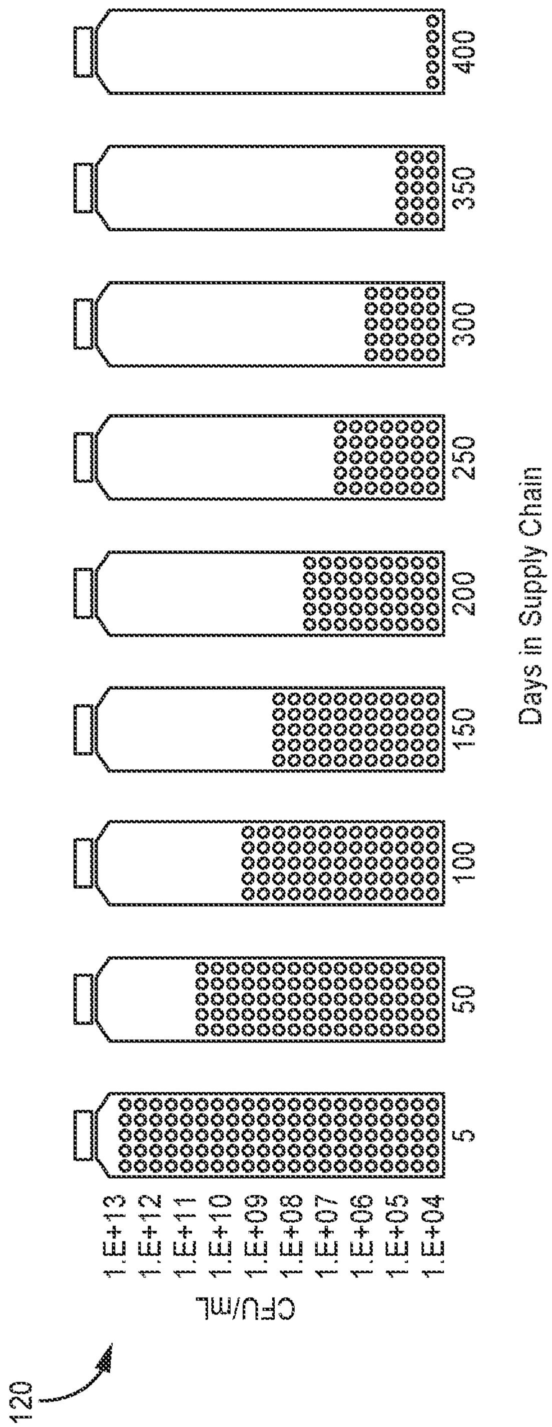
FIG. 1B illustrates a diagrammatic chart of microorganism viability compared to days in the supply chain, according to some embodiments.

FIG. 1B illustrates a diagrammatic chart 120 of microorganism viability compared to days in the supply chain 100, according to some embodiments. The number of microbial cells within the biologic agricultural product that are viable (CFU/mL) decreases exponentially as the biologic agricultural product ages in the supply chain. Therefore, it would be beneficial to reduce the amount of time that the microbial cells are suspended in the solution of the biologic agricultural product to deliver a higher concentration of viable microorganisms to the crops and/or soil.

Embodiments of the present disclosure reduce the amount of time that microbial cells are suspended in the solution of a biologic agricultural product. For instance, the microorganisms may be manufactured and stored separate from the suspension solution. The microorganisms may be stabilized in an inactive state, for example, by storing the stabilized microbial culture in a form selected from one or more of: planktonic, biofilmic, dormant, lyophilized, partially dormant, partially lyophilized, sporulated, dehydrated, spray-dried, fluidized-bed dried and/or freeze-dried to inhibit microbial activity. The stabilized microorganisms may be reactivated (i.e., rehydrated and/or re-vitalized to initiate one or more cellular functions of the microorganisms) directly before the in-field use stage 110. Thus, the stabilized microorganisms may be substantially preserved through the manufacturing storage stage 104, the distribution stage 106, and the on-farm storage stage 108. Thus, viable microorganisms may be applied to crops and/or soil within minutes of rehydration and are not subject to the exponential decrease in microbe viability caused by storage and delivery time in the supply chain 100.

Figure 2:
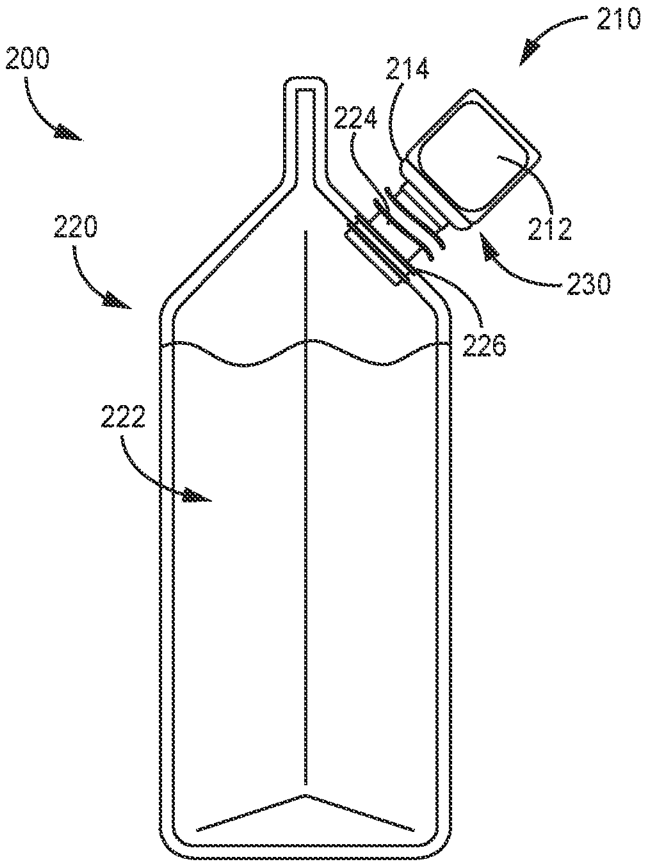
FIG. 2 illustrates an exploded cross-sectional side view of a microorganism activation system 200 for activating microorganisms prior to application of microorganisms to agricultural products, according to some embodiments.

FIG. 2 illustrates an exploded cross-sectional side view of a microorganism activation system 200 for activating microorganisms prior to application of microorganisms to agricultural products, according to some embodiments. The microorganism activation system 200 includes a first container 210, a second container 220, and a disruptable dividing member 230.

The first container 210 may contain a stabilized microbial culture 212 therein. The stabilized microbial culture 212 may be in a form selected from one or more of: planktonic, biofilmic, dormant, lyophilized, partially dormant, partially lyophilized, sporulated, dehydrated, spray-dried, fluidized-bed dried, and freeze-dried. The stabilized microbes are not present in a log phase growth while in the stabilized form.

The stabilized microbial culture 212 (i.e., stabilized microbes or stabilized microorganisms) may be selected from the group comprising one or more of: bacteria, yeast, fungi, algae, protozoa, and nematodes. For example, the microorganisms can comprise one or more of: *Achromobacter, Actimomycetes, Arthrobacter, Azospirillum, Azotobacter, Bacillus, Bradyrhizobium*, Chromobacterium, Cyanobacteria, *Enterobacter, Gliocladium, Klebsiella, Lysobacter, Methylobacterium, Mitsuaria, Paenibacillus, Pasteuria, Pseudomonas, Rhizobium, Serratia*, and *Streptomyces*. In other embodiments, the microbes can comprise one or more of: *Penicillium, Trichoderma, Chaetomium*, mycorrhizal fungi, and those forming ectomycorrhizae and vesicular-arbuscular mycorrhizae; mycoparastic fungi, nematode-trapping fungi, avirulent isolates of pathogenic fungi or bacteria. In one embodiment, the microbes can comprise one or more of: 2,4-diacetylphloroglucinol (DAPG)-producing bacteria; and ph1D+*Pseudomonas* spp. Also, in certain embodiments, the microorganism can be derived from yield improving indigenous soil microflora from a predetermined location. The microorganisms can be genetically engineered or genetically modified for improved biocontrol activity, improved nutrient accessibility to crops, improved nitrogen-fixing ability, improved phytohormone production, improved activation of nitrogen assimilation, improved rhizosphere adaptation, improved competitiveness, and/or improved metal chelation ability.

The second container 220 may include an aqueous rehydration solution 222 therein. The aqueous rehydration solution 222 may include one or more of water, non-chlorinated water, distilled water, Luria broth, phosphate buffered saline (PBS) solution, trypticase soy broth (TSB) solution, skim milk, non-fat skim milk solution, sucrose solution, peptone solution, and/or a nutrient broth.

The aqueous rehydration solution 222 promotes microbial viability without promoting microbial growth (i.e., without fermentation and without log phase microbial growth). The aqueous rehydration solution 222 may inhibit log growth and/or maintain the rehydrated microbes in a lag phase. In some cases, the aqueous rehydration solution 222 lacks a nutritive carbon source, a nutritive nitrogen source, or lacks both nutritive carbon and nutritive nitrogen sources. Thus, the aqueous rehydration solution 222 re-initiates cellular functions of the microorganism (e.g., synthesize RNA, synthesize enzymes, synthesize essential metabolites, adjust to environmental conditions, undertake repair of injured cells, etc.) without initiating fermentation of the microorganisms. The conditions of the second chamber 220 may be selectively controlled to prevent fermentation/log phase growth via an oxygen scavenge and/or nitrogen purge. Because fermentation/log phase growth is not a necessary part of the rehydration process, the rehydrated microbes can be applied to crops/soil mere minutes or hours after the stabilized microbial culture 212 contacts the aqueous rehydration solution 222.

The aqueous rehydration solution 222 may include one or more inducers blended with an inert carrier or a dispersing aid. A solid formulation can comprise 25-99.9% by weight inducer(s) and 0.1-75% formulation aids. The second container 220 can have a volume capable of receiving and mixing the contents of the first container 210 to a desired concentration (e.g., as a concentrate, emulsion concentrate, concentrated suspension (e.g., tank mix), or to the final "ready-to-use" concentration (e.g., field mix)). In some embodiments, a ratio of the volume of the first container 210 to the volume of the second container 220 may be approximately 1:10, and in some embodiments the ratio may be within a range between 1:10 and 1:100. In some cases, the kit further includes (c) a third container (e.g., an intermediate chamber 330) holding or configured to hold an agronomically-acceptable carrier. The third container can be pre-filled with the agronomically-acceptable carrier or configured for filling at the end-user location (e.g., where water is the agronomically-acceptable carrier and have a volume capable of receiving and mixing the contents of the first container 210. In some embodiments, a ratio of the volume of the third container to the volume of the first container 210 may be within a range of between 10:1 and 2:1. In some embodiments, a ratio of the volume between the third container and the second container 220 may be within a range of between 1:5 and 1:50. In embodiments where the kit includes the third container, the ratio of the volume of the first container 210 to the volume of the second container 220 may be approximately 1:100. The kit can be provided with printed instructions for adding and mixing the contents of the containers, rehydration of the stabilized microbial culture, and optionally for the on-demand dispersion, suspension, dissolution, or reconstitution of the aqueous rehydration solution 222.

In some embodiments, the aqueous rehydration solution 222 may include a metabolite inducer, wherein the inducer is selected from a group consisting of inducers of microbial phytohormone biosynthesis, inducers of nitrogen assimilation pathways, inducers of microbial osmoadaptation pathways, inducers of microbial biological control factor biosynthesis, inducers of microbial infection and nodule growth in plant root tissue. The inducer can increase production of at least one of the group of microbial secondary metabolites consisting of metabolites capable of auxin production, metabolites capable nitrogen fixation, metabolites capable production of an antimicrobial compound, metabolites capable mineral phosphate solubilization, metabolites capable siderophore production, metabolites capable cellulase production, metabolites capable chitinase production, metabolites capable xylanase production, and metabolites capable acetoin production. The inducer can be selected from the group consisting of inorganic salts, sodium nitrate, sodium chloride, metal enzyme cofactors, Co, Fe, Zn, Fe, Al, Cu, amino acids, branched amino acids, choline, carnitine, tryptophan, ornithine, leucine, methionine, proline, valine, lysine, phenylalanine, glycine, tyrosine, arginine, N,N'-dimethylglycine, ethanol, γ-butyrolactones, N-acylhomoserine lactones, oligopeptides of Gram-positive bacteria, B-factor (3'-(1-butylphosphoryl) adenosine), A-factor (2-S-isocapryloyl-3R-hydroxymethyl-γ-butyrolactone), virginiae butanolides, N-(B-ketocaproyl)-Lhomoserine lactone (KHL), plant flavonoids, plant isoflavonoids, genistein, daidzein hesperetin, and naringenin.

The disruptable dividing member 230 may separate the stabilized microbial culture 212 located within the first container 210 from the aqueous rehydration solution 222 located within the second container 220. In some embodiments, the disruptable dividing member 230 may be secured to the first container 210. The disruptable dividing member 230 may be tearable, frangible, puncturable, rupturable, dissolvable, movable, or combinations thereof. Disrupting the disruptable dividing member 230 may create a flow path between the first container 210 and the second container 220.

In some embodiments, the first container 210 may include a first attachment member 214 and the second container 220 may include a second attachment member 224 disposed within a port 226. The first attachment member 214 may be removably securable to the second attachment member 224. In some embodiments, securing the first attachment member 214 to the second attachment 224 may disrupt the disruptable member 230 and form a flow path between the first container 210 and the second container 220. In some embodiments, the second attachment mechanism 224 may be removably secured to the port 226.

The flow path formed between the first container 210 and the second container 220 may allow the stabilized microbial culture 212 to flow into the second container 220 and contact the aqueous rehydration solution 222. In other embodiments, the flow path formed between the first container 210 and the second container 220 may allow the aqueous rehydration solution 222 to flow through the flow path and into the first container 210 and contact the stabilized microbial culture.

In some embodiments, contact between the stabilized microbial culture 212 and the aqueous rehydration solution 222 rehydrates the microorganisms within the stabilized microbial culture and thereby re-initiates cellular activity of the microorganisms. The stabilized microbial culture 212 may include microorganisms in an inactive or dormant state. Contact between the stabilized microbial culture 212 and the aqueous rehydration solution 222 may provide an aqueous solution to the microorganisms and may permeate the cell membranes of the microorganisms to rehydrate the microorganisms. Upon rehydration, the microorganisms may resume cellular activity and/or basic cellular functions.

The stabilized microbial culture 212 may contain dead microorganisms, injured microorganisms, and unharmed microorganisms, as the preservation technique (e.g., freeze drying or lyophilization) may damage a portion of the microorganisms. Furthermore, stabilized preparations of microbes may suffer considerable mortality during rehydration from osmotic shock and/or hypertonic conditions leading to cellular burst or apoptosis. Thus, to maximize viability of the rehydrated microorganisms, the contact between the stabilized microbial culture 212 and the aqueous rehydration solution 222 may occur under controlled conditions. For example, in cases where the rehydration solution solely comprises water, the viability rate of rehydrated microbes is typically less than 50% (e.g., for *Candida sake*, the viability rate was between 8-27% and for *Lactobacillus* spp, the viability rate was between 6-51%). The aqueous rehydration solution 222 provides viability rate greater than 50%, and in some embodiments, the aqueous rehydration solution 222 generates a viability rate of 75% or greater.

Figure 3:
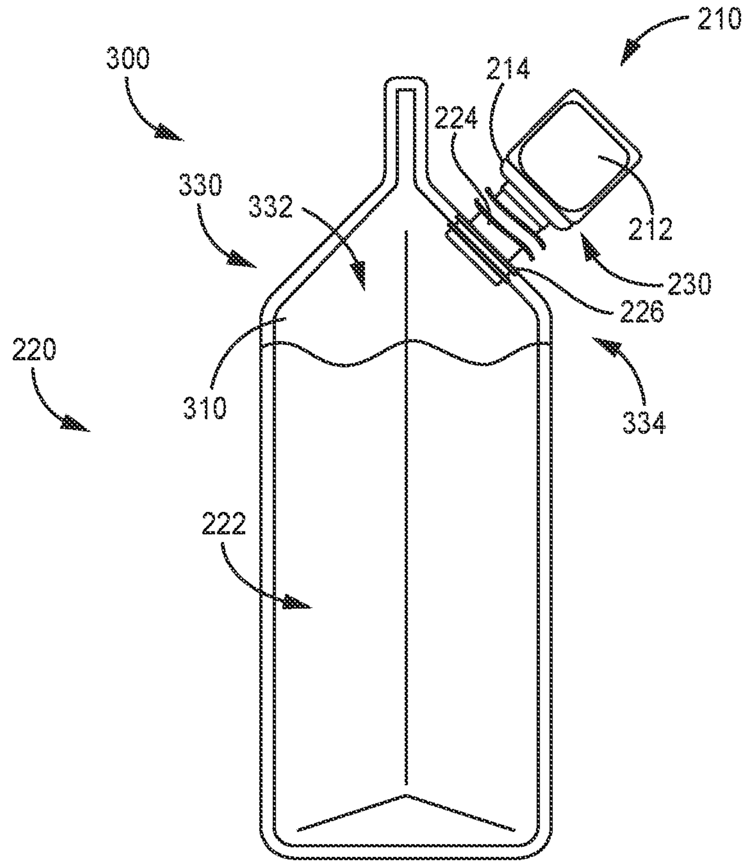
FIG. 3 illustrates an exploded cross-sectional side view of a microorganism activation system for activating microorganisms prior to application of microorganisms to agricultural products, according to some embodiments.

FIG. 3 illustrates an exploded cross-sectional side view of a microorganism activation system 300 for activating microorganisms prior to application of microorganisms to agricultural products, according to some embodiments. The microorganism activation system 300 includes the first container 210, the second container 220, and the disruptable dividing member 230.

In some embodiments, the microorganism activation system 300 may include a second dividing member 310. The second dividing member 310 may form an intermediate chamber 330 within the microorganism activation system 300 positioned between the first container 210 and the second container 220. The second dividing member may be in mechanical communication with a release mechanism 334. Actuation of the release mechanism 334 may disrupt the second dividing member 310 and form a flow path between the intermediate chamber 330 and the second container 220. In some embodiments, the intermediate chamber 330 may be formed within the second container. The intermediate chamber 330 may include a priming solution 332 configured to prepare the microorganisms for rehydration.

In some embodiments, a volume of the priming solution 332 in the intermediate chamber 330 may be less than the volume of the aqueous rehydration solution 222 in the second container. The lower volume of the priming solution 332 may be beneficial, as microorganism vitality may be increased with lower volumes of aqueous solutions. The lower volume of aqueous solution may prevent rapid movement of aqueous liquid through the cell membrane, which if occurring at high rates, may cause cellular rupture or apoptosis. In some embodiments, the intermediate chamber may provide a partial rehydration to the microorganisms wherein the microorganisms are partially revived and/or primed for full rehydration. The multi-stage rehydration process (i.e., partial rehydration in the intermediate chamber 330 and full rehydration in the second container 220) may improve microbe vitality by preventing osmotic shock and cellular burst.

In some embodiments, a first mass of the priming solution 332 may be approximately equal to a second mass of the stabilized microbial culture 212. The first mass to second mass ratio may be referred to hereinafter as a priming solution to microbe ratio. In some embodiments, the priming solution to microbe ratio may be between 10:1 and 2:1. In other embodiments, the priming solution to microbe ratio may be greater than 10:1.

In some embodiments, a first volume of the aqueous rehydration solution 222 may be greater than a second volume of the priming solution 332. The first volume to second volume ratio may be between 2:1 and 50:1, and in some embodiments, the first volume to second volume ratio may be between 5:1 and 20:1. In some embodiments, the first volume to second volume ratio may be approximately 10:1.

In some embodiments, the priming solution 332 may include one or more inducers (or activators of microbial gene pathway) to catalyze a microbial secondary metabolism. The inducer can be a precursor of a secondary metabolite, a cofactor of an enzyme involved in secondary metabolite biosynthesis, a natural or synthetic regulator of one or more synthases of a biosynthetic pathway, or a natural or synthetic regulator of gene expression. The inducer can be a substrate for an enzyme involved in secondary metabolite biosynthesis (e.g., a precursor), a cofactor of an enzyme involved in secondary metabolite biosynthesis (e.g., an inorganic ion or coenzyme), a natural or synthetic regulator of one or more synthases of a biosynthetic pathway, or a natural or synthetic regulator of gene expression. In some cases, the rehydration medium can include a mixture of inducers, e.g., inducing the same secondary metabolic pathway or inducing different secondary metabolic pathways. In some cases, at least one inducer is selected from the group consisting of inducers of phytohormone biosynthesis (e.g., auxin, ethylene (ET), abscisic acid, cytokinin, brassinosteroid, salicylic acid, jasmonic acid and/or gibberellin biosynthesis inducers), inducers of nitrogen assimilation activation (e.g., inorganic salts (e.g., sodium nitrate or sodium chloride), inducers of osmoadaptation pathways (e.g., glycine betaine, carnitine and/or proline accumulation inducers), inducers of biological control factor biosynthesis (e.g., VOC production, antimicrobial compound, phenazine, pyrrolnitrin, hydrogen cyanide, and/or siderophore biosynthesis inducers), inducers of infection and nodule growth in plant root tissue (e.g., lipo-chitin-oligosaccharide biosynthesis inducers). Inducers of biocontrol of plant pathogens can induce secondary metabolites such as antibiotics (2,4-diacetylephloroglucinol, phenazines, cyclic lipopeptides), competitive uptake of plant exudates/leachates, lytic enzymes (e.g., chitinases, glucanases, proteases), waste product release (ammonia, carbon dioxide, hydrogen cyanide), siderophore activity, molecular cross-talk, and phytohormone-mediated induction of host resistance. The inducer can be selected for its ability to activate production of one or more specific secondary metabolites, such as a secondary metabolite capable of auxin production, nitrogen fixation, production of an antimicrobial compound, mineral phosphate solubilization, siderophore production, cellulase production, chitinase production, xylanase production, or acetoin production.

The concentration of inducer in the rehydration composition will depend on the microbial culture and the desired secondary metabolite. An effective concentration of inducer can be determined empirically by detecting the level of the secondary metabolite induced within a given period of time. The rehydration composition can comprise a working concentration of inducer(s) within a range of about 0.001% to about 20% w/v of the composition. For example, the ready-to-use rehydration composition can include about 0.01% to 15% w/v, about 0.05% to 12% w/v, about 0.1% to 10% w/v, about 0.25% to 5% w/v, about 0.45% to 2% w/v, or about 0.5-1% w/v.

The priming solution 332 can include at least two inducers. The at least two inducers can induce the same secondary metabolism pathway or different secondary metabolism pathways. The at least one inducer can be selected from the group consisting of inducers of microbial phytohormone biosynthesis, inducers of nitrogen assimilation pathways, inducers of microbial osmoadaptation pathways, inducers of microbial biological control factor biosynthesis, inducers of microbial infection and nodule growth in plant root tissue. The at least one inducer can increase production of at least one of the group of microbial secondary metabolites consisting of metabolites capable of auxin production, metabolites capable nitrogen fixation, metabolites capable production of an antimicrobial compound, metabolites capable mineral phosphate solubilization, metabolites capable siderophore production, metabolites capable cellulase production, metabolites capable chitinase production, metabolites capable xylanase production, and metabolites capable acetoin production. The at least one inducer can be selected from the group consisting of inorganic salts, sodium nitrate, sodium chloride, metal enzyme cofactors, Co, Fe, Zn, Fe, Al, Cu, amino acids, branched amino acids, choline, carnitine, tryptophan, ornithine, leucine, methionine, proline, valine, lysine, phenylalanine, glycine, tyrosine, arginine, N,N'-dimethylglycine, ethanol, γ-butyrolactones, N-acylhomoserine lactones, oligopeptides of Gram-positive bacteria, B-factor (3'-(1-butylphosphoryl) adenosine), A-factor (2-S-isocapryloyl-3R-hydroxymethyl-γ-butyrolactone), *virginiae* butanolides, N-(β-ketocaproyl)-Lhomoserine lactone (KHL), plant flavonoids, plant isoflavonoids, genistein, daidzein hesperetin, and naringenin.

The intermediate chamber 330 may include a dual-function to initiate the rehydration process under controlled conditions (i.e., the partial rehydration or multi-stage rehydration process) and to activate one or more microbial gene pathways with the inducer(s) in the priming solution 332. The intermediate chamber may improve microorganism viability through the rehydration process.

Figure 4A:
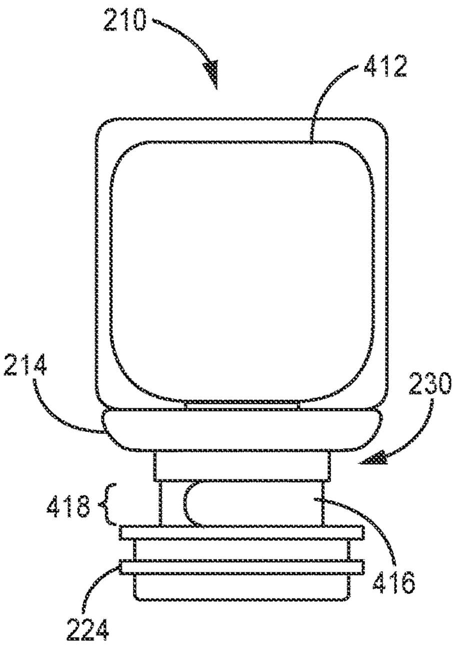
FIG. 4A illustrates a side view of the first container removably secured to the second attachment member of the second container, according to some embodiments.
Figure 4B:
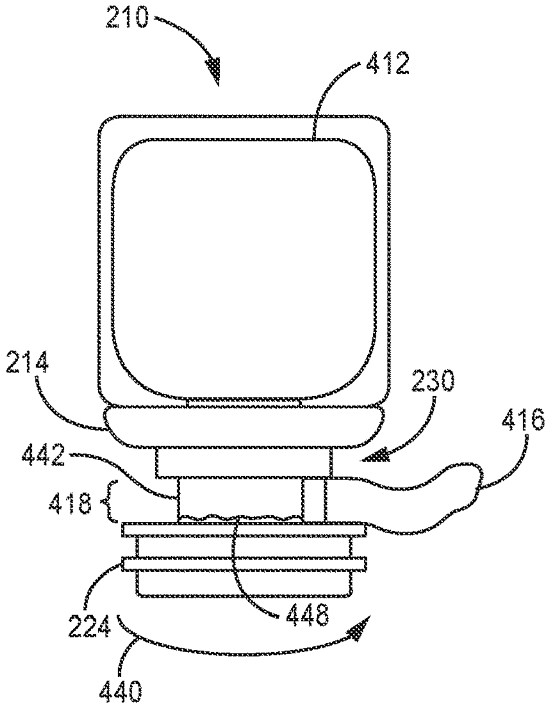
FIG. 4B illustrates a side view of the first container removably secured to the second attachment member of the second container, according to some embodiments.
Figure 4C:
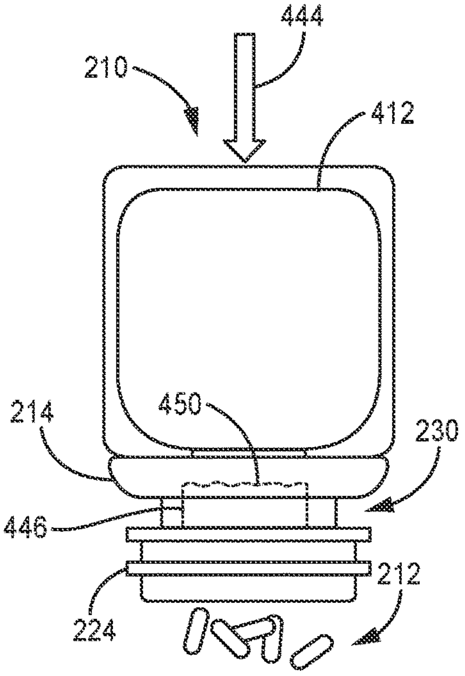
FIG. 4C illustrates a side view of the first container removably secured to the second attachment member of the second container, according to some embodiments.

FIGS. 4A-C illustrate side views of the first container 210 removably secured to the second attachment member 224 of the second container 220, according to some embodiments. The first container 210 may include an inner pouch 412 containing the stabilized microbial culture 212. The inner pouch 412 may be a foil pouch with an impermeable membrane to keep moisture and other outside contaminants from entering the foil pouch. In some embodiments, the inner pouch 412 may undergo an oxygen scavenge and/or a nitrogen purge to remove growth initiating compounds from the inner pouch 412 and thereby keep the stabilized microbial culture 212 in an inactive state (i.e., removing all activation elements from the inner pouch 412). The inner pouch 412 may include the dividing member 230. The dividing member 230 may be tearable, frangible, puncturable, rupturable, dissolvable, movable, and/or combinations thereof.

FIG. 4A illustrates the first container 210 with a spacing member 416 positioned between the first attachment member 214 from the second attachment member 224. The spacing member 416 may maintain a gap 418 between the first attachment member 214 and the second attachment member 224. FIG. 4B illustrates the spacing member 416 being removed from the first container 210 as the spacing member is unwound in direction 440. The spacing member 416 may be wound around a first annular member 442. The first annular member 442 may be receivable within the second attachment member 224, and in some embodiments, the first annular member 442 may include a first cutting surface 448.

FIG. 4C illustrates the first container 210 forced in direction 444 toward the second attachment member 224. The second attachment member 224 may include a second annular member 446. The second annular member 446 may include a second cutting surface 450. In some embodiments, the second cutting surface may tear, puncture, rupture and/or move the dividing member 230 to allow the stabilized microbial culture 212 to flow therethrough. The first annular member 442 may be forced into the second attachment feature 224 and the second annular member 446 may be forced into the first attachment feature 214. The first annular member 442 and the second annular member 446 may include different diameters to allow one annular member to be received within the circumference of the other member (i.e., the first annular member 442 and the second annular member 446 may be positioned concentric to each other). The stabilized microbial culture 212 may flow out from the inner pouch and through both of the first annular member 442 and the second annular member 446 to the second container 220. The concentric alignment of the first annular member 442 and the second annular member 446 may provide aseptic delivery (i.e., free from outside contamination) of the stabilized microbial culture 212 to the second container 220.

In some embodiments, the first attachment member 214, the spacing member 416, and the second attachment member 224 may be shipped together in an assembly. The second attachment member 224 may be removably securable to the port 226 of the second container 220, and thus, the combined assembly may be removably secured to the port 226. In some embodiments, a plurality of the assemblies (the first attachment member 214, the spacing member 416, and the second attachment member 224) may be selectively attached and removed to the second container 220 to rehydrate a plurality of different microbial cultures within the second container simultaneously (or sequentially). In some embodiments, the second container 220 may include a plurality of ports 226 to rehydrate a plurality of different microbial cultures. In some embodiments, each of the plurality of ports 226 may be fluidically connected to a unique (i.e., unshared) intermediate chamber for partial rehydration and/or inducing gene pathways of the microbial culture.

Figure 5:
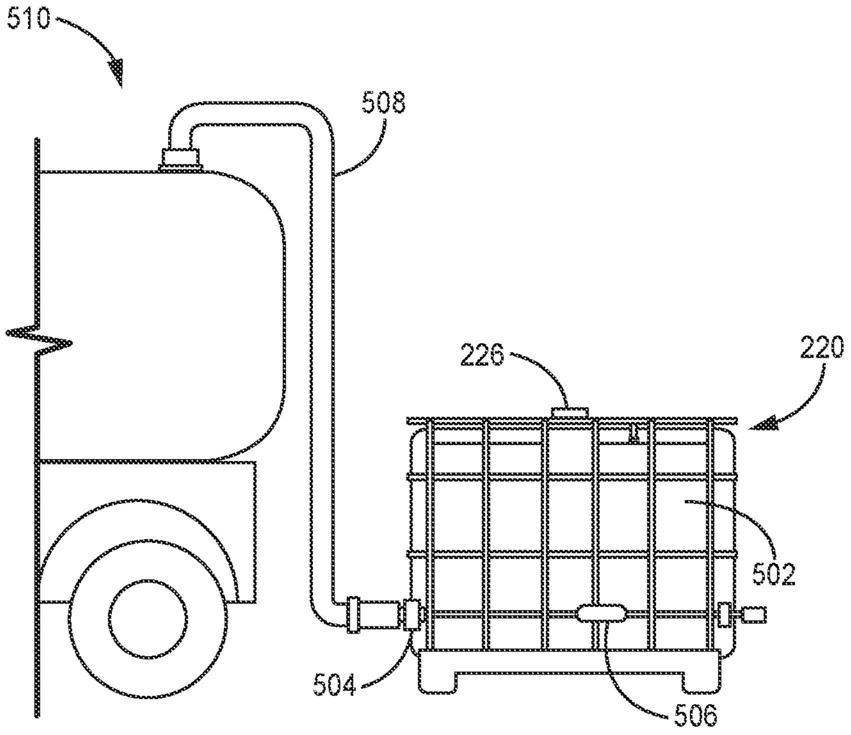
FIG. 5 illustrates the second container transferring a rehydrated microbial solution to an agricultural applicator, according to some embodiments.

FIG. 5 illustrates the second container 220 transferring a rehydrated microbial solution 502 to an agricultural applicator 510, according to some embodiments. The second container 220 may include a fluid transfer port 504 configured to removably secure a tube 508 secured to the agricultural applicator 510. The second container 220 may include a fluid agitation mechanism 506 configured to agitate and/or mix the rehydrated microbial solution 502. In some embodiments, agitation of the aqueous rehydration solution 220 subsequent to the introduction of the stabilized microbial culture may improve rehydration rate and/or viability rate of the microorganisms. The agitation mechanism 506 may include movable mechanical components (e.g., a movable whisk or whip) and in some embodiments, may include a pump to move liquid around the second container 220.

The agricultural applicator 510 may include an agricultural sprayer (e.g., a fertilizer sprayer, a pesticide sprayer, an insecticide sprayer, an herbicide sprayer, etc.) configured to spray the rehydrated microbial solution 502 onto agricultural crops and/or soil. The agricultural applicator 510 may include an agricultural spreader configured to spread the rehydrated microbial solution 502 across agricultural crops and/or soil. Thus, the rehydrated microbes may be applied to an agricultural plant. For example, the agricultural plant may comprise one or more of: *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., Sorghum spp., *Miscanthus* spp., *Saccharum* spp., Erianthus spp., *Populus* spp., *Andropogon* gerardii (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Arundo donax* (giant reed), *Secale cereale* (rye), Salix spp. (willow), *Eucalyptus* spp. (*eucalyptus*), Triticosecale spp. (*triticum*-wheat X rye), Bambuseae (Bamboo), Carthamus tinctorius (safflower), Jatropha curcas (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassaya), *Lycopersicon esculentum* (tomato), *Lactuca* saliva (lettuce), Musa paradisiaca (banana), *Solanum tuberosum* (potato), *Brassica oleracea* (broccoli, cauliflower, brusselsprouts),

*Camellia sinensis* (tea), Fragaria *ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis* saliva, Camptotheca acuminate, Catharanthus *roseus, Vinca rosea, Cinchona officinalis, Coichicum autumnale, Veratrum californica, Digitalis lanata, Digitalis purpurea, Dioscorea* spp., Andrographis *paniculata, Atropa belladonna, Datura stomonium, Berberis* spp., Cephalotaxus spp., Ephedra *sinica*, Ephedra spp., Erythroxylum coca, *Galanthus* wornorii, Scopolia spp., Lycopodium *serratum* (Huperzia *serrata*), Lycopodium spp., Rauwolfia *serpentina*, Rauwolfia spp., *Sanguinaria canadensis, Hyoscyamus* spp., *Calendula officinalis, Chrysanthemum parthenium, Coleus forskohlii, Tanacetum parthenium, Parthenium* argentatum (guayule), Hevea spp. (rubber), *Mentha spicata* (mint), *Mentha piperita* (mint), *Bixa orellana*, Alstroemeria spp., Rosa spp. (rose), *Dianthus* caryophyllus (carnation), *Petunia* spp. (*petunia*), Poinsettia *pulcherrima* (poinsettia), *Nicotiana tabacum* (tobacco), *Lupinus albus* (lupin), *Uniola paniculata* (oats), *Agrostis* spp. (bentgrass), *Populus tremuloides* (aspen), *Pinus* spp. (pine), *Abies* spp. (fir), Acer spp. (maple), *Hordeum vulgare* (barley), *Poa pratensis* (bluegrass), *Lolium* spp. (ryegrass), *Phleum pratense* (timothy), and conifers. The plant or plant part can be selected from energy crops, optionally, cellulose-based energy crops, starch-based energy crops, sugar-based energy crops and biofuel-producing energy crop.

Promoting plant growth can include disease resistance, drought tolerance, heat tolerance, cold tolerance, salinity tolerance, metal tolerance, herbicide tolerance, chemical tolerance, improved water use efficiency, improved nitrogen utilization, improved nitrogen fixation, pest resistance, herbivore resistance, pathogen resistance, increase in yield, increase in yield under water-limited conditions, health enhancement, germination efficiency, vigor improvement, growth improvement, photosynthetic capability improvement, nutrition enhancement, altered protein content, altered oil content, increase in biomass, increase in shoot length, increase in root length, improved root architecture, increase in seed weight, altered seed carbohydrate composition, altered seed oil composition, increase in radical length, number of seed pods, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, increase in number of seed pods per plant, increase in length of seed pods per plant, reduced number of wilted leaves per plant, reduced number of severely wilted leaves per plant, increase in number of non-wilted leaves per plant, and improved plant visual appearance, or any combination thereof.

Figure 6:
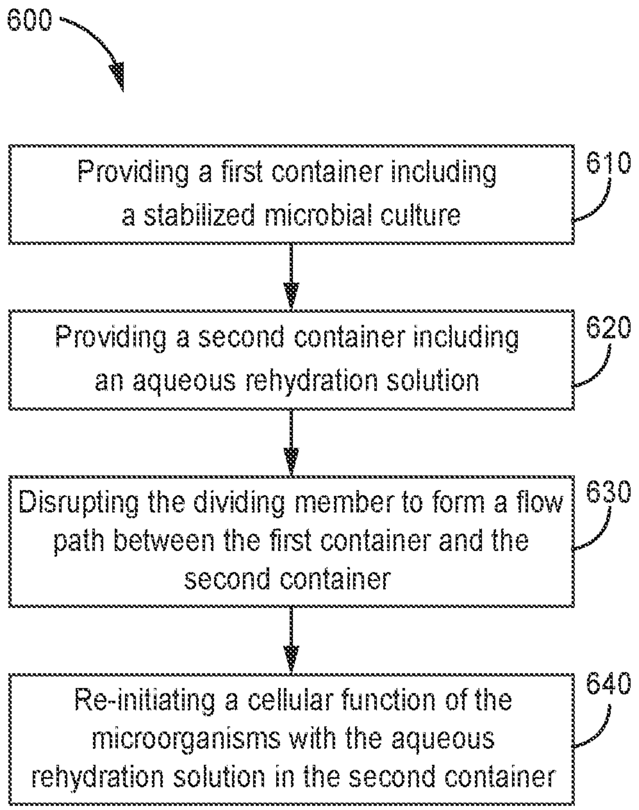
FIG. 6 illustrates a flow chart of a method for delivering viable microorganisms to an agricultural applicator, according to some embodiments.

FIG. 6 illustrates a flow chart of a method for delivering viable microorganisms to an agricultural applicator, according to some embodiments.

The method 600 may include step 610, providing a first container including a stabilized microbial culture. The first container may include any or all of the features of the first container 210 discussed above with respect to FIGS. 2-5. The stabilized microbial culture may include any or all features of the stabilized microbial culture 212 discussed above with respect to FIGS. 2-5.

The method 600 may include step 620, providing a second container including an aqueous rehydration solution. The second container may include any or all of the features of the second container 220 discussed above with respect to FIGS. 2-5. The aqueous rehydration solution may include any or all features of the aqueous rehydration solution 222 discussed above with respect to FIGS. 2-5. In some embodiments, the second container 220 may include the intermediate chamber 330 including the priming solution 332.

The method 600 may include step 630, disrupting the dividing member 230 to form a flow path between the first container 210 and the second container 220. The dividing member 230 may be formed from the first container 210, may be formed from the second container 220, or may be a separate element therebetween. In some embodiments, disrupting the dividing member 230 may include urging the first container 210 toward the second container 220 to cut, tear, rupture, or otherwise break the inner pouch 414 of the first container 210. In some embodiments, disrupting the dividing member 230 may form a flow path between the first container 210 and the second container 220. The stabilized microbial culture 212 may travel through the combined flow path to contact the aqueous rehydration solution 222 in the second container 220.

The method 600 may include step 640, re-initiating a cellular function of the microorganisms with the aqueous rehydration solution 222 in the second container 220. In some embodiments, contact between the stabilized microbial culture 212 and the aqueous rehydration solution 222 may result in the aqueous rehydration solution 222 permeating through membranes of the microorganisms to re-introduce water into the microorganism cellular structures. In some embodiments, re-initiating a cellular function of the microorganisms may include initiating a lag-phase of microbial activity wherein microbes synthesize RNA, enzymes, and/or essential metabolites, as well as adjust to environmental conditions in the second container and undertake necessary repair of injured cells.

In some embodiments, step 640 may include introducing the stabilized microbial culture 212 to an intermediate chamber 330 including a priming solution 332. The priming solution 332 may be configured to prepare the microorganisms for rehydration, i.e., the priming solution may partially rehydrate the microorganisms and introduce gene pathway activators to induce microbial expression of desired genes to boost viability and performance. The multi-stage rehydration process (i.e., partial rehydration in the intermediate chamber and full rehydration in the second container) may improve microbe vitality by preventing osmotic shock/cellular burst by controlling the rate at which aqueous solution permeates the cellular membrane.

In some embodiments, the method 600 may include agitating the aqueous rehydration solution and the microorganisms in the second container. Agitation of the microorganisms may improve rehydration rate and/or viability rate of the microorganisms. The method may include transferring the rehydrated microbial solution 502 to an agricultural applicator (e.g., the agricultural applicator 510).

In some embodiments, the method 600 may include transporting the first container 210 with the stabilized microbial culture 212 separate from the aqueous rehydration solution 222. The method 600 may include storing the first container 210 with the stabilized microbial culture 212 separate from the aqueous rehydration solution 222. The method 600 may include waiting to disrupt the dividing member 230 until a time for delivering the microorganisms to the agricultural applicator 510.

The above Detailed Description includes references to the accompanying drawings, which form a part of the Detailed Description. The Detailed Description should be read with reference to the drawings. The drawings show, by way of illustration, specific embodiments in which the present devices, systems, and methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the Detailed Description and accompanying drawings. Also, various features or components have been or can be grouped together to streamline the disclosure. This should not be interpreted as intending that an unclaimed disclosed feature is essential to any claim. Rather, inventive subject matter can lie in less than all features of a disclosed embodiment. Thus, the following claims are hereby incorporated into the Detailed Description, with each example standing on its own as a separate embodiment.

Certain terms are used throughout this patent document to refer to features or components. Different people may refer to the same feature or component by different names. This patent document does not intend to distinguish between components or features that differ in name but not in function.

The scope of the present devices, systems, and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, system, or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An apparatus for delivering viable microorganisms in an agricultural applicator, the apparatus comprising:
- a first container including a stabilized microbial culture therein;
- a second container including an aqueous rehydration solution disposed therein; and
- a disruptable dividing member separating the stabilized microbial culture in the first container from the aqueous rehydration solution in the second container,
- wherein disrupting the dividing member forms a flow path between the first container and the second container to allow contact between the stabilized microbial culture and the aqueous rehydration solution, and
- wherein contact between the stabilized microbial culture and the aqueous rehydration solution re-initiates lag phase cellular activity of the viable microorganisms.

2. The apparatus of claim 1 further comprising:
- a transfer port fluidically connected to the second container,
- wherein the viable microorganisms are transferred to the agricultural applicator through the transfer port, and
- wherein the agricultural applicator dispenses the viable microorganisms on agricultural seeds, plants, and/or soil.

3. The apparatus of claim 1, wherein the stabilized microbial culture include microbes selected from a group consisting of: *Achromobacter, Actimomycetes, Arthrobacter, Azospirillum, Azotobacter, Bacillus, Bradyrhizobium*, Chromobacterium, Cyanobacteria, *Enterobacter, Gliocladium, Klebsiella, Lysobacter, Methylobacterium, Mitsuaria, Paenibacillus, Pasteuria, Pseudomonas, Rhizobium, Serratia, Streptomyces, Penicillium, Trichoderma, Chaetomium*, mycorrhizal fungi, ectomycorrhizae, vesicular-arbuscular mycorrhizae, mycoparastic fungi, nematode-trapping fungi, avirulent isolates of pathogenic fungi or bacteria, 2,4-diacetylphloroglucinol (DAPG)-producing bacteria, and/or ph1D+*Pseudomonas* spp.

4. The apparatus of claim 3, wherein the stabilized microbial culture is in a form selected from one or more of: planktonic, biofilmic, dormant, lyophilized, partially dormant, partially lyophilized, encapsulated, sporulated, dehydrated, spray-dried, fluidized-bed dried and/or freeze-dried to inhibit microbial activity.

5. The apparatus of claim 1, wherein the aqueous rehydration solution is selected from a group consisting of: water, non-chlorinated water, distilled water, Luria broth, phosphate buffered saline (PBS) solution, non-fat skim milk solution, sucrose solution, peptone solution, trypticase soy broth (TSB) solution, and/or a nutrient broth.

6. The apparatus of claim 1, wherein the first container includes a first attachment member and wherein the second container includes a second attachment member, wherein the first attachment member is removably securable to the second attachment member, and wherein attachment of the first attachment member to the second attachment member disrupts the dividing member to form a flow path between the first container and the second container.

7. The apparatus of claim 6, wherein the first attachment member and the second attachment member are annular and include apertures therethrough, wherein securing the first attachment member to the second attachment member thereby aligns the apertures to form the flow path, and wherein the second attachment member includes an annular cutting surface to disrupt the dividing member.

8. The apparatus of claim 1 further comprising:
- an intermediate chamber positioned between the first container and the second container, the intermediate chamber including an inducer,
- wherein the inducer induces a gene response in the viable microorganisms to promote microbial viability.

9. The apparatus of claim 8, wherein the inducer is selected from an inducer group consisting of:
- inducers of phytohormone biosynthesis, including auxin, ethylene (ET), abscisic acid, cytokinin, brassinosteroid, salicylic acid, jasmonic acid and/or gibberellin;
- inducers of nitrogen assimilation activation including inorganic salts, sodium nitrate and/or sodium chloride;
- inducers of osmoadaptation pathways including glycine betaine, carnitine and/or proline accumulation inducers;
- inducers of biological control factor biosynthesis including VOC production, the inducers of biological control factor biosynthesis including an antimicrobial compound, phenazine, pyrrolnitrin, hydrogen cyanide, and/or siderophore biosynthesis inducers, and/or inducers of infection and nodule growth in plant root tissue including lipo-chitin-oligosaccharide biosynthesis inducers.

10. The apparatus of claim 1, wherein the first container includes a first volume and the second container includes a second volume, wherein a ratio of the second volume to the first volume is less than or equal to 10:1.

11. The apparatus of claim 1, wherein the first container includes a foil pouch sealed to isolate the stabilized microbial culture from external conditions, wherein the foil pouch is resistant to humidity, wherein the foil pouch includes an oxygen scavenger and a nitrogen purge, and wherein the dividing member comprises one or more walls or surfaces of the first chamber, and wherein the dividing member is tearable, frangible, puncturable, rupturable, dissolvable, movable, or combinations thereof.

12. The apparatus of claim 1, wherein the aqueous rehydration solution includes between 0.1% and 10% trypticase soy broth (TSB) solution to reduce osmotic stress on the stabilized microbial culture.

* * * * *